(12) United States Patent
Mali et al.

(10) Patent No.: US 6,969,511 B1
(45) Date of Patent: Nov. 29, 2005

(54) SYNTHETIC BULK LAXATIVE

(75) Inventors: Subhash Pandurang Mali, Maharashtra (IN); Srinivasan Sarangan, Maharashtra (IN); Rajan Vitthal Gupte, Maharashtra (IN); Jayant Venkatesh Deshpande, Maharashtra (IN); Kamlesh Jayantilal Ranbhan, Maharashtra (IN)

(73) Assignee: Kopran Research Laboratories Ltd., Maharashtra Seoul (IN)

( * ) Notice: Subject to any disclaimer, the term of this patent is extended or adjusted under 35 U.S.C. 154(b) by 314 days.

(21) Appl. No.: 10/130,780

(22) PCT Filed: Jun. 29, 2000

(86) PCT No.: PCT/IN00/00064

§ 371 (c)(1),
(2), (4) Date: May 21, 2002

(87) PCT Pub. No.: WO02/00226

PCT Pub. Date: Jan. 3, 2002

(51) Int. Cl.$^7$ ............................................. A61K 9/02
(52) U.S. Cl. ................... 424/78.01; 424/435; 424/451; 424/464
(58) Field of Search .................. 424/78.08, 78.17, 424/78.01, 451, 464, 435

(56) References Cited

U.S. PATENT DOCUMENTS

| | | | |
|---|---|---|---|
| 2,923,692 A * | 2/1960 | Ackerman et al. .......... 524/548 |
| 3,997,484 A | 12/1976 | Weaver et al. ............. 260/17.4 |
| 4,070,348 A | 1/1978 | Kraemer et al. ........... 260/79.3 |
| 4,076,663 A | 2/1978 | Masuda et al. ............ 260/17.4 |
| 4,267,103 A | 5/1981 | Cohen ....................... 260/17.4 |
| 4,535,098 A | 8/1985 | Evani et al. ................ 521/149 |
| 4,618,631 A | 10/1986 | Takeda et al. .............. 521/109 |
| 4,777,232 A | 10/1988 | Heidel ........................ 527/300 |
| 4,931,497 A | 6/1990 | Engelhardt et al. ........... 525/42 |
| 5,011,892 A | 4/1991 | Engelhardt et al. ......... 525/404 |
| 5,221,722 A | 6/1993 | Sehm ...................... 526/230.5 |
| 5,340,853 A | 8/1994 | Chmelir et al. ............... 524/56 |
| 5,354,290 A | 10/1994 | Gross ......................... 604/367 |
| 5,514,754 A | 5/1996 | Henderson et al. ......... 525/296 |
| 5,626,154 A | 5/1997 | Rogers et al. .............. 132/200 |
| 5,716,707 A | 2/1998 | Mukaida et al. ............ 428/402 |
| 5,804,605 A | 9/1998 | Palumbo ...................... 521/28 |
| 5,973,014 A | 10/1999 | Funk et al. ................... 521/64 |
| 5,985,944 A | 11/1999 | Ishizaki et al. ............... 521/64 |

FOREIGN PATENT DOCUMENTS

| | | |
|---|---|---|
| EP | 0 050 347 | 4/1982 |
| EP | 0 105 634 | 4/1984 |
| EP | 0 346 097 | 12/1989 |
| FR | 2717815 | 9/1995 |
| JP | 6322178 | 11/1994 |

* cited by examiner

Primary Examiner—Jyothsna Venkat
(74) Attorney, Agent, or Firm—Ladas & Parry LLP

(57) ABSTRACT

A synthetic bulk laxative which comprises a crosslinked graft polymer. It is formed of a hydrophilic monomer partially neutralized up to 75%, a polysaccharide gum up to 3% by weight and a crosslinker up to 2% by weight. The weight percentages are with respect to the hydrophilic monomer. A process for the preparation of the synthetic bulk laxative which comprises up to 75% partial neutralization of a hydrophilic monomer with an alkali. The partially neutralized hydrophilic monomer is polymerized with up to 2% by weight of a cross linker and up to 3% by weight of a polysaccharide gum in the presence of an initiator in an organic solvent under inert atmosphere at 30–80° C. The synthetic bulk laxative is dried at 30–120° C. and pulverized. A formulation of the synthetic bulk laxative in combination with pharmaceutically acceptable excipients.

30 Claims, No Drawings

SYNTHETIC BULK LAXATIVE

This invention also relates to a process for the preparation of the synthetic bulk laxative and a formation comprising the same.

BACKGROUND ART

Laxatives are classified depending on their mechanisms of action. For example, laxatives comprising preparations of sodium phosphate or magnesium sulfate are of the osmotic type. Laxatives comprising preparations of phenolphthalein, bisacodyl, danthron, senna or cascara are of stimulant type and laxative comprising preparations of docusates, poloxamer, mineral oil or castor oil are of surfactant type. The osmotic, stimulant and surfactant laxatives have limited use due to their non-acceptable organoleptic properties and poor efficacy.

Yet another type of laxative is bulk laxative which on oral administration swells significantly occupying most of the intestinal lumen, thereby improving gastrointestinal motility to cure constipation. Bulk laxative is also used in the treatment of diarrhoea. Bulk laxative may comprise semi-synthetic polymers such as calcium polycarbophil or methyl cellulose or natural products such as bran, psyllium or isphagula husk. Due to the low swellability of calcium polycarbophil ie calcium substituted polymer formed of acrylic acid monomer and a crosslinker under physiological conditions, it is required to be prescribed in high doses of 4–6 g/day (ie 8–12 tablets of 500 mg/day). Methyl cellulose also has limited use due to its high dosage requirement (6 gm/day). Amongst the bulk laxatives, isphagula husk is most widely used. It exhibits low swelling (~40 times) in simulated intestinal fluid (USP 23 Page No 2053) and necessitates administration of large doses (7 gm/day) which causes discomfort and results in loss of appetite. Besides swelling in the intestine, isphagula husk also significantly swells in the stomach occupying a large volume and causes abdominal pain and discomfort. Proteins associated with the natural product isphagula husk are known to cause sensitisation of the mucous membrane, irritation and other allergic reactions in the body. Isphagula husk has low dispersibility in water because of which it forms lumps or agglomerates in aqueous fluids. The lumps swell non-uniformly and adversely affect gastrointestinal motility. Moreover, being a natural product, isphagula husk is prone to microbial contamination during storage.

U.S. Pat. No. 4,777,232 describes such polymers comprising water soluble monomers such as acrylic acid or methacrylic acid and a polysaccharide such as starch or derivative thereof. It is formed in combination with a surface active agent and employs the polysaccharide in an amount of 10–70% by weight of the monomer. U.S. Pat. No. 3,997,484 discloses a graft polymer formed of polyacrylonitrile and gelatinised starch as polysaccharide. Graft polymers of acrylic monomers such as acrylonitrile with polysaccharide such as starch or cellulose derivative are known (U.S. Pat. Nos. 4,076,663, 4,931,497 and 5,011,892). U.S. Pat. No. 5,340,853 describes a mixture of 20–98%, preferably 10–50% by weight of a polymer such as polyacrylic acid, polymethacrylic acid, polyacrylamide or polymethacrylamide and 2–80%, preferably 10–50% by weight of a polysaccharide such as tragacanth or guar gum, gum arabic, starch, dextran, cellulose or derivative thereof. Polymers comprising polysaccharides are reported to find applications in diapers, sanitary napkins, tampons, surgical pads and sheets, paper towels, electrolyte thickeners in dry batteries, moisture conserving materials in agriculture or drying agents. The polymers of the above US Patents are not known or reported to have been used as laxative. Due to gelatinisation of starch, the polymers will show low swellability (30 to 40 times) in physiological fluids though their swellability in water is high. The starch in such graft polymers is likely to undergo digestion in the physiological fluid, and reduce the swellability of the graft polymers. Moreover such polymers are not slimy. High percentages of polysaccharides in polymer have been found to reduce the swellability thereof in physiological fluids.

Crosslinked, water soluble, water absorbable or water swellable polymers formed of monomers such as acrylates, acrylic acids, acrylamides, acrylonitriles or vinyl pyrrolidones and cross linkers are known and reported to be used as absorbing or dehydrating or thickening agents in sanitary napkins, diapers, shaving system or for bioadhesion (U.S. Pat. Nos. 5,985,944, 4,070,348, 5,354,290, 5,716,707, 5,804,605, 4,618,631, 5,514,754, 5,626,154, 4,535,098, 5,973,014, 5,221,722 and 4,267,103; EP Patent No 105634B1 and JP Patent No 6322178A).

Gums such as tragacanth, acacia or xanthan gum are water swellable and are known to be used as emulsifiers, binders, stabilisers, thickening or suspending agents in food and pharmaceutical industry.

DISCLOSURE OF THE INVENTION

An object of the invention is to provide a synthetic bulk laxative, which shows high swelling in the physiological fluids and is slimy and assists bowel movement.

Another object of the invention is to provide a synthetic bulk laxative, which has less swelling in stomach than in the intestine and eliminates abdominal pain and discomfort.

Another object of the invention is to provide a synthetic bulk laxative, which may be administered in low doses of 1–2 gm/day.

Another object of the invention is to provide a synthetic bulk laxative, which does not cause mucous membrane sensitisation, irritation or other allergic reactions.

Another object of the invention is to provide a synthetic bulk laxative, which does not form lumps or agglomerates and swells uniformly.

Another object of the invention is to provide a synthetic bulk laxative, which is non-absorbable in the intestinal fluid.

Another object of the invention is to provide a synthetic bulk laxative, which is inert and non-susceptible to microbial contamination during storage.

Another object of the invention is to provide a process for the preparation of a synthetic bulk laxative, which results in a product having high swelling in the physiological fluids and is slimy to assist bowel movement.

Another object of the invention is to provide a process for the preparation of a synthetic bulk laxative, which results in a product having less swelling in stomach than in the intestine and thus eliminating abdominal pain and discomfort.

Another object of the invention is to provide a process for the preparation of a synthetic bulk laxative, which results in a product that may be administered in low doses of 1–2 gm/day.

Another object of the invention is to provide a process for the preparation of a synthetic bulk laxative, which results in a product that does not cause mucous membrane sensitisation, irritation or other allergic reactions.

Another object of the invention is to provide a process for the preparation of a synthetic bulk laxative, which results in a product that does not form lumps or agglomerates and swells uniformly.

Another object of the invention is to provide a process for the preparation of a synthetic bulk laxative, which results in a product that is non-absorbable in the intestinal fluid.

Another object of the invention is to provide a process for the preparation of a synthetic bulk laxative, which results in an inert product non-susceptible to microbial contamination during storage.

Another object of the invention is to provide a formulation of a synthetic bulk laxative, which has high swelling in physiological fluid and is slimy and assists bowel movement.

Another object of the invention is to provide a formulation of a synthetic bulk laxative, which has less swelling in stomach than in the intestine and eliminates abdominal pain and discomfort.

Another object of the invention is to provide a formulation of a synthetic bulk laxative, which may be administered in low doses of 1–2 gm/day.

Another object of the invention is to provide a formulation of a a synthetic bulk laxative, which does not cause mucous sensitisation, irritation or other allergic reactions.

Another object of the invention is to provide a formulation of a synthetic bulk laxative, which does not form lumps or agglomerates and swells uniformly.

Another object of the invention is to provide a formulation of a synthetic bulk laxative, which is non-absorbable in the intestinal fluid.

Another object of the invention is to provide a formulation of a synthetic bulk laxative, which is inert and non-susceptible to microbial contamination during storage.

According to the invention there is provided a synthetic bulk laxative comprising a crosslinked graft polymer formed of a hydrophilic monomer partially neutralised upto 75%, a polysaccharide gum upto 3% by weight and a crosslinker upto 2% by weight; the weight percentages being with respect to the hydrophilic monomer.

According to the invention there is also provided a process for the preparation of a synthetic bulk laxative comprising:
a) upto 75% partial neutralisation of a hydrophilic monomer with an alkali;
b) polymerisation of the partially neutralised hydrophilic monomer with a crosslinker upto 2% by weight and a polysaccharide gum upto 3% by weight, in the presence of an initiator in an organic solvent under inert atmosphere at 30–80° C., the weight percentages being with respect to the hydrophilic monomer;
c) drying the synthetic bulk laxative at 30–120° C.; and
d) pulverising the dried synthetic bulk laxative.

According to the invention there is also provided a formulation of a synthetic bulk laxative comprising a crosslinked graft polymer formed of a hydrophilic monomer partially neutralised upto 75%, a polysaccharide gum upto 3% by weight and a crosslinker upto 2% by weight, the weight percentages being with respect to the hydrophilic monomer, mixed with pharmaceutically acceptable excipients.

Preferably the polysaccharide gum is in 0.05–0.1% by weight and preferably the cross linker is in 0.01 to 0.5% by weight.

The hydrophilic monomer may be selected from a group comprising acrylic acid, methacrylic acid, 2-ethyl hexyl acrylic acid, hydroxy ethyl acrylic acid or hydroxy ethyl methacrylic acid, acrylamide, methacrylamide, vinyl pyrrolidone, acrylonitile or methacrylonitrile. Preferably acrylic acid may be used.

The polysaccharide gum used for grafting may be mucilaginous and selected from preferably acacia, xanthan or tragacanth gum.

The crosslinker may be divinyl benzene, ethylene glycol dimethacrylate, methylene bis acrylamide, methylene bis methacrylamide, allyl glycidyl ether or such other compounds known in the art. Preferably ethylene glycol dimethacrylate, divinyl benzene or allyl glycidyl ether may be used.

Preferably 20–30% partial neutralisation of the hydrophilic monomer may be carried out prior to polymerisation.

The alkali used for neutralisation may be selected from sodium hydroxide, carbonate or bicarbonate, potassium hydroxide, carbonate or bicarbonate, or calcium, magnesium or aluminium hydroxide. Preferably potassium hydroxide or carbonate or calcium hydroxide may be used.

The initiator may be ammonium peroxide, benzoyl peroxide, azobis isobutyronitrile, lauroyl peroxide or such other compounds known in the art, preferably benzoyl peroxide and may be used in 0.5–1.5% by weight of the hydrophilic monomer.

The polymerisation is preferably carried out at 60–80° C.

The organic solvent may be ethyl acetate, isopropyl acetate, butyl acetate, acetone or methyl isobutyl ketone or a mixture thereof, preferably 1:1::ethyl acetate:acetone.

The inert atmosphere may be nitrogen or argon, preferably nitrogen.

The synthetic bulk laxative may be dried at preferably 50–70° C.

The dried synthetic bulk laxative obtained may be pulverized in known manner to uniform powder of 40/120 mesh size.

The pulverised synthetic bulk laxative of the invention may be formulated into tablets, capsules, sachets, biscuits, wafers or other oral dosage forms, using pharmaceutically acceptable excipients such as saccharin, microcrystalline cellulose, magnesium stearate, aspartame, flavours or other such compounds known in the art in known manner.

The synthetic graft polymer bulk laxative comprising a hydrophilic monomer chemically bonded to a polysaccharide gum and crosslinker in the weight percentages as defined in the invention exhibits high swelling (~100 times) in physiological ie intestinal fluid. The polymer of the invention has mucilagonous slimy texture and assists bowel movement and cures constipation. The polysaccharide gum does not undergo digestion in the physiological fluid and is non-absorbable. Therefore there is no deterioration in swellability of the graft polymer of the invention in physiological fluids on oral ingestion. Due to their high swellability, the polymers of the invention can be conveniently administered in small doses of 1–2 gm/day to be effective. The polymers show relatively less swelling in acidic gastric fluid (6–12 times) than in the intestinal fluid and therefore do not cause pain and abdominal discomfort. The graft polymer laxative of the invention is highly dispersible in the intestinal fluids. Therefore the polymer does not form lumps or agglomerates and swells uniformly invivo. The polymer of the invention is synthetically prepared and hence is not associated with allerginic protein. Therefore mucous membrane sensitisation, irritation or allergic reactions are not caused with the use of this polymer. Since the polymer is not a natural product but is synthetically made, it is resistant to microbial attack and is not prone to contamination during storage.

Due to the water-swellable property, the polymer of the invention besides as a laxative, may be used in the treatment of diarrhoea and to regulate consistency of effluent in colostomy patients or as a constituent element of sanitary napkins, tampons, paper diapers, wound protecting/healing materials, biological carrier or moisture conserving materials in agriculture.

The following experimental examples are illustrative of the invention but not limitative of the scope thereof.

EXAMPLE 1

Acrylic acid (25.0 gm) was neutralised with potassium carbonate (4.5 g). To this tragacanth gum (0.125 gm) was added. Divinyl benzene (0.6 gm) in ethyl acetate and acetone mixture (1:1, 100.0 ml) and benzoyl peroxide (300.0 mg) were added to the above mixture and the mixture was polymerised by refluxing under nitrogen atmosphere for 6 hours at 60° C. The reaction mass was filtered and dried at 50° C. for 8 hours to obtain 24.5 gm of the crosslinked acrylic acid-tragacanth gum graft polymer.

EXAMPLE 2

The procedure of Example 1 was followed using 0.75 gm instead of 0.6 gm of divinyl benzene to obtain 24.1 gm of crosslinked acrylic acid-tragacanth gum graft polymer.

EXAMPLE 3

The procedure of Example 1 was followed using 0.85 gm instead of 0.6 gm of divinyl benzene to obtain 24.8 gm of crosslinked acrylic acid-tragacanth gum graft polymer.

EXAMPLE 4

The procedure of Example 3 was followed using 0.125 gm instead of 0.85 gm of divinyl benzene and without tragacanth gum to obtain 23.9 gm of the crosslinked acrylic acid polymer.

EXAMPLE 5

The procedure of Example 4 was followed using 0.25 gm instead of 0.125 gm of divinyl benzene to obtain 25.1 gm of the crosslinked acrylic acid polymer.

EXAMPLE 6

The procedure of Example 4 was followed using 0.5 gm instead of 0.125 gm of divinyl benzene to obtain 23.9 gm of the crosslinked acrylic acid polymer.

EXAMPLE 7

The procedure of Example 1 was followed using 0.125 gm instead of 0.6 gm of divinyl benzene and 1.0 gm instead of 0.125 gm of tragacanth gum to obtain 24.5 gm of the crosslinked acrylic acid-tragacanth gum graft polymer.

EXAMPLE 8

The procedure of Example 7 was followed using 1.2 gm instead of 1.0 gm of tragacanth gum to obtain 24.8 gm of the crosslinked acrylic acid-tragacanth gum graft polymer.

EXAMPLE 9

The procedure of Example 7 was followed using 1.5 gm instead of 1.0 gm of tragacanth gum to obtain 24.3 gm of the crosslinked acrylic acid-tragacanth gum graft polymer.

EXAMPLE 10

The procedure of Example 7 was followed using 0.08 gm instead of 0.125 gm of divinyl benzene and 0.03 gm instead of 1.0 gm of tragacanth gum to obtain 25.6 gm of crosslinked acrylic acid-tragacanth graft polymer.

EXAMPLE 11

The procedure of Example 7 was followed using 0.1 gm instead of 0.125 gm of divinyl benzene and using 0.125 gm instead of 1.0 gm of tragacanth gum to obtain 23.5 gm of crosslinked acrylic acid-tragacanth gum graft polymer.

EXAMPLE 12

The procedure of Example 7 was followed using 0.375 gm instead of 1.0 gm of tragacanth gum to obtain 24.1 gm of crosslinked acrylic acid-tragacanth gum graft polymer.

The polymers of Examples 1 to 12 were pulverised and passed through sieve of mesh size 52 and polymer powders of mesh size 85 were retained.

EXAMPLE 13

A sachet weighing 1.5 gm was prepared by mixing the following ingredients:

| | |
|---|---|
| Graft polymer of Example 12 | 1.0 g |
| Citric acid | 0.2 g |
| Aspartame | 0.1 g |
| Lemon juice flavour | 0.2 g |

EXAMPLE 14

Tablets were obtained by mixing the following ingredients before compressing.

| | |
|---|---|
| Graft polymer of Example 12 | 500.0 mg |
| Hydroxypropyl cellulose (L-HPC) | 30.0 mg |
| Colloidal silica | 2.0 mg |
| Apricot flavour | 1.0 mg |
| Vanilla flavour | 1.0 mg |
| Saccharin | 0.1 mg |
| Magnesium stearate | 0.1 mg |

EXAMPLE 15

Hard gelatin capsules were prepared by mixing the following ingredients and filling into capsules:

| | |
|---|---|
| Graft polymer of Example 12 | 500.0 mg |
| Magnesium stearate | 5.0 mg |
| Microcrystalline cellulose | 50.0 mg |

SWELLABILITY TESTS

Swellability tests were carried out on the polymers of Examples 1 to 12 in simulated gastric juice (pH 1.5) and simulated intestinal fluid (pH 7.5) as per the USP method (USP 23 page no 2053). Polymers of Examples 7 to 12 were tested for swellability in bicarbonate solution (pH 8.5) as per the method used for testing the swellability of calcium polycarbophil (Product literature of B F Goodrich and Company) and the results were as follows in Table 1:

TABLE 1

| | Swell weight in gm/gm of polymer | | |
|---|---|---|---|
| Polymer | Pepsin solution (pH 1.5) | Pancreatin solution (pH 7.5) | Bicarbonate solution (pH 8.5) |
| Example 1 | 2.4 | 50.8 | — |
| Example 2 | 2.1 | 33.4 | — |
| Example 3 | 2.0 | 20.5 | — |
| Example 4 | 8.3 | 76.1 | — |
| Example 5 | 10.1 | 72.5 | — |
| Example 6 | 11.5 | 62.6 | — |
| Example 7 | 2.8 | 60.0 | 111.0 |
| Example 8 | 3.6 | 55.5 | 102.6 |
| Example 9 | 3.9 | 45.0 | 83.2 |
| Example 10 | 7.5 | 89.5 | 165.5 |
| Example 11 | 8.6 | 93.8 | 173.53 |
| Example 12 | 9.1 | 95.0 | 175.53 |
| Calcium polycarbophil | 4.60 | 45.00 | 38.00 |
| Isphagula husk | 30.00 | 37.85 | 17.10 |

The results of polymers of Examples 4 to 6 when compared to those of Examples 10 to 12 show that the polymers of the invention with the polysaccharide gum incorporated thereinto show high swelling when compared to the polymers without the polysaccharide gum. The results of polymers of Examples 1 to 3 and Examples 7 to 9 show that higher weight percentages of the crosslinker and the polysaccharide gum in the polymer than those defined in the invention, reduce the swelling capacity thereof. Swelling of the polymers of Examples 10 to 12 in pancreatin being ~10 times more than that in pepsin, the polymers of the invention will exhibit less swelling in the stomach than in the intestine. An observation of the swollen polymers of Examples 10 to 12 showed uniformity in the swelling. This shows that the polymers of the invention do not form lumps or agglomerates. The polymers of the invention show better swellability when compared to isphagula and calcium polycarbophil.

Sliminess Test

A blind study was conducted to determine the sliminess by sense of touch of the polymers of Examples 1 to 12, polycarbophil and isphagula by handing over the pancreatin solution swollen polymers of Examples 1 to 12, calcium-polycarbophil and isphagula to 10 adult volunteers. The evaluation was conducted on the basis of 4 ratings viz 0 for non-slimy, 1 for slightly slimy, 2 for moderately slimy and 3 for highly slimy feel. The analysis rated the polymers of Examples 10 to 12 and isphagula at 3. The polymers of Examples 1 to 3 were rated 2. The polymers of Examples 4 to 6 and calcium polycarbophil were rated 1.

The results show that the polymers of the invention are very slimy when compared to the other polymers and calcium polycarbophil.

In vivo Studies

In vivo studies were conducted using the polymers of the invention, the details of which are as follows:

Wistar albino rats weighing between 180–200 g of either sex were divided into 3 groups consisting of 8 animals each and were housed individually as 3 animals per cage. The distribution of animals in groups, the sequence of trials and the treatment alloted to each group were randomized. The treatment was that the 1st group i.e. control group received phosphate buffer saline [1 ml/kg; per oral (p.o.)], the 2nd group received polymer of Example 12 (70 mg/kg; p.o.) and the 3rd group received isphagula husk (70 mg/kg; p.o.) and was continued for 7 consecutive days, 30 minutes after administration of either the drug or saline, all the animals were hydrated by administering 5 ml of water by oral route and fed with standard rat chow diet (20 g/rat).

I) Gastro-intestinal Motility Test

Following treatment, the rats were fasted for 18 h. To each animal was administered orally, 1 ml of charcoal meal (3% deactivated charcoal in 10% aqueous tragacanth). 1 hour later, each animal was killed and the distance moved by the charcoal meal in the intestine from the pylorus was cut and measured and expressed as a percentage of the distance from the pylorus to the caecum and the results are as in Table 2.

TABLE 2

| Treatment (mg/kg × days) | Total length (cm) | Movement of charcoal meal (cm) | Movement of charcoal meal (%) |
|---|---|---|---|
| Control | 83.52 ± 9.67 | 47.58 ± 4.66 | 52.81 ± 2.21 |
| Example 12 (70 × 7) | 84.50 ± 4.53 | 66.50 ± 5.32 | 82.63 ± 4.84 |
| Isphagula husk (70 × 7) | 82.25 ± 6.62 | 61.32 ± 5.98 | 73.39 ± 5.93 |

Polymer of Example 12 showed improved bowel movement and its results were found to be statistically significant ($P<0.01$). This also proves the high slimy nature of the polymer of the invention.

II) Castor-oil Induced Diarrhoea in Rats

The method followed here was the method of Awouters et al (1978) with modification. The rats were fasted for 18 hours before being treated. One hour later each animal received 1 ml of castor oil orally by gavage and then observed for defacation upto 4 hours and the presence of characteristic diarrhoeal droppings were noted in the transparent plastic dishes placed beneath the individual rate cages. The results were as shown in Table 3.

TABLE 3

| Oral pretreatment at 1 h (mg/kg × days) | Mean defacations/group | Mean no of wet faeces/group |
|---|---|---|
| Control | 4.32 ± 0.82 | 4.32 ± 0.82 |
| Example 12 (70 × 7) | 2.03 ± 0.63 | 1.16 ± 0.21 |
| Isphagula husk (70 × 7) | 2.36 ± 0.34 | 1.85 ± 0.32 |

Polymer of Example 12 showed good control on diarrhoea with reduced wetness in faecal matter as shown in Table 3 and these results were found to be statistically significant ($P<0.01$).

III) Radiological Testing for Laxative Action: Materials and Methods

Wistar albino rats of either sex weighing between 160–220 g were used in this study. The animals were divided into four groups. Animals from all groups were housed individually in standard cages with filter paper at the bottom on which a mesh of the same size was placed. The animal was placed on the mesh to avoid coprophasy and for proper collection of faecal matter. The laxative activity was studied over a period of 11 days. From day 1 to 5, ie predosing period, each animal is provided with 20 g of food and water (ad libitum per day). From day 5 to 10 the animals received their respective treatment at the same everyday orally as follows:

Rats of group I served as control i.e. they were fed with 2 ml water, group II was treated with isphagula husk (70 mg/kg body weight/day in 2 ml water), group III with calcium polycarbophil (80 mg/kg body weight/day in 2 ml water) and group IV with polymer of Example 10 (25 mg/kg body weight/day in 2 ml water).

After 4 days treatment all the animals were fasted overnight and on the next day the animals were subjected to X-rays after 0.5, 2 and 24 hours to study the intestinal transit (motility), after feeding the animals with barium meal (2 ml/rat). The appearance of barium, a radio opaque substance, in different parts of the gastro intestinal tract was observed and the results were as shown in Table 4.

TABLE 4

| | Appearance of barium after | | |
|---|---|---|---|
| Group | 0.5 hr | 2 hrs | 24 hrs |
| I | Mid ileum | Mid ileum | Traces |
| II | Proximal colon | — | Traces |
| III | Distal ileum | Descending colon | Traces |
| IV | Descending colon | Rectum | Traces |

Polymer of the invention showed better laxative property compared to isphagula husk and calcium polycarbophil, since within 30 mins the polymer of the invention showed a bowel movement upto descending colon whereas use of isphagula husk and calcium polycarbophil showed bowel movements upto proximal colon and distal ileum respectively. In addition, use of polymer of the invention showed well maintained barium column, whereas in case of isphagula husk and calcium polycarbophil, the column was broken, which presumably indicates erratic contractions of the intestine and thus abdominal discomfort. Thus the polymer of the invention is a more effective laxative, at a lower dose of 25 mg/kg body weight/day dose when compared to isphagula and calcium polycarbophil at higher doses of 70 mg/kg weight/day and 80 mg/kg weight/day respectively.

At the end of X-ray studies, the water content in the faecel matter from all the groups was determined and the results were as follows in Table 5.

TABLE 5

| Group | Water content (%) | Average length of faecal dropping (mm) | Average width of faecal dropping (mm) | Bulk volume (ml/gm) |
|---|---|---|---|---|
| I | 49 | 15 | 5 | 1.2 |
| II | 61.5 | 16 | 6 | 1.2 |
| III | 63.4 | 16 | 6 | 1.2 |
| IV | 71.2 | 17 | 7 | 2.4 |

The faeces of Group IV appeared significantly bulkier than those of Groups I, II and III.

CONCLUSION

The above observations suggest that polymer of the invention improved the consistency of the faeces (softens the faeces) and increased the gastro-intestinal motility comparable to that of isaphgula and are capable of being used as bulk laxatives and that too at one-third dose. The polymers of the invention solidified the faeces and reduced its water content and can also be used in the treatment of diarrhoea.

What is claimed is:

1. A synthetic bulk laxative comprising a crosslinked graft polymer formed from a hydrophilic monomer partially neutralised up to 75%, a polysaccharide gum up to 3% by weight of the hydrophilic monomer and a crosslinker up to 2% by weight of the hydrophilic monomer.

2. A bulk laxative as claimed in claim 1, wherein the hydrophilic monomer is 20–30% partially neutralised.

3. A bulk laxative as claimed in claim 1, wherein the hydrophilic monomer is acrylic acid.

4. A bulk laxative as claimed in claim 1, wherein the polymer is formed with the polysaccharide gum in an amount of 0.05–0.1% by weight of the hydrophilic monomer.

5. A bulk laxative as claimed in claim 1, wherein the polysaccharide gum is acacia, tragacanth or xanthan gum.

6. A bulk laxative as claimed in claim 1, wherein the polymer is formed with the cross linker in an amount of 0.01 to 0.5% by weight of the hydrophilic monomer.

7. A bulk laxative as claimed in claim 1, wherein the crosslinker is ethylene glycol dimethacrylate, divinyl benzene or allyl glycidyl ether.

8. A process for the preparation of a synthetic bulk laxative comprising:
 a) partially neutralizing up to 75% of a hydrophilic monomer with an alkali;
 b) polymerizing the partially neutralized hydrophilic monomer with a polysaccharide gum in an amount of up to 2% by weight of the hydrophilic monomer in the presence of a cross linker in an amount of up to 2% by weight of the hydrophilic monomer and an initiator in an organic solvent under inert atmosphere at 30–80° C. to form a graft polymer,
 c) drying the graft polymer at 30–120° C.; and
 d) pulverizing the dried graft polymer.

9. A process as claimed in claim 8, wherein the hydrophilic monomer is acrylic acid.

10. A process as claimed in claim 8, wherein the hydrophilic monomer is partially neutralized up to 20–30%.

11. A process as claimed in claim 8, wherein the alkali is potassium bicarbonate.

12. A process as claimed in claim 8, wherein the graft polymer is formed with the cross linker in an amount of 0.02 to 0.5% by weight of the hydrophilic monomer.

13. A process as claimed in claim 8, wherein the crosslinker is ethylene glycol dimethacrylate, divinyl benzene or allyl glycidyl ether.

14. A process as claimed in claim 8, wherein the graft polymer is formed with the polysaccharide gum in an amount of 0.05–0.1% by weight of the hydrophilic monomer.

15. A process as claimed in claim 8, wherein the polysaccharide gum is acacia, tragacanth or xanthan gum.

16. A process as claimed in claim 8, wherein the initiator is benzoyl peroxide.

17. A process as claimed in claim 8, wherein the organic solvent is 1:1::ethyl acetate:acetone mixture.

18. A process as claimed in claim 8, wherein the polymerisation is carried out at 60° C.

19. A process as claimed in claim 8, wherein the inert atmosphere is nitrogen.

20. A process as claimed in claim 8, wherein the graft polymer is dried at 50° C.

21. A formulation of a synthetic bulk laxative comprising (a) a crosslinked graft polymer formed from a hydrophilic monomer partially neutralised up to 75%, a polysaccharide gum up to 3% by weight of the hydrophilic monomer and a crosslinker up to 2% by weight of the hydrophilic monomer, and (b) a pharmaceutically acceptable excipient.

22. A formulation as claimed in claim 21, wherein the hydrophilic monomer is partially neutralised up to 20–30%.

23. A formulation as claimed in claim 21, wherein the hydrophilic monomer is acrylic acid.

24. A formulation as claimed in claim 21, wherein the polymer is formed with the polysaccharide gum in an amount of 0.05–0.1% by weight of the hydrophilic monomer.

25. A formulation as claimed in claim 21, wherein the polysaccharide gum is acacia, tragacanth or xanthan gum.

26. A formulation as claimed in claim 21, wherein the polymer is formed with the cross linker in an amount of 1.01 to 0.5% by weight of the hydrophilic monomer.

27. A formulation as claimed in claim 21, wherein the crosslinker is ethylene glycol dimethacrylate, divinyl benzene or allyl glycidyl ether.

28. A formulation as claimed in claim 21, which is in the form of a tablet, capsule, sachet, biscuit or wafer.

29. The bulk laxative of claim 1, wherein the graft polymer is formed with respective amounts of the polysaccharide gum and the cross-linker effective to increase a swelling capacity of the graft polymer as compared with the polymer without the polysaccharide gum.

30. The process of claim 8, wherein the graft polymer is formed with respective amounts of the polysaccharide gum and the cross-linker effective to increase a swelling capacity of the graft polymer as compared with the polymer without the polysaccharide gum.

* * * * *